United States Patent [19]

Johnson et al.

[11] Patent Number: 5,144,034

[45] Date of Patent: Sep. 1, 1992

[54] PROCESS FOR THE SYNTHESIS OF CYCLOPENTENE DERIVATIVES OF PURINES

[75] Inventors: M. Ross Johnson, Chapel Hill; Michael R. Peel, Durham; Daniel D. Sternbach, Chapel Hill, all of N.C.

[73] Assignee: Glaxo Inc., Research Triangle Park, N.C.

[21] Appl. No.: 505,969

[22] Filed: Apr. 6, 1990

[51] Int. Cl.$^5$ .................. C07D 473/18; C07D 473/40
[52] U.S. Cl. .................... 544/276; 544/277; 556/418
[58] Field of Search ................ 544/276, 277

[56] References Cited

U.S. PATENT DOCUMENTS

| | | | |
|---|---|---|---|
| 4,916,224 | 4/1990 | Vince et al. | 544/254 |
| 4,931,559 | 6/1990 | Vince et al. | 544/276 |
| 4,950,758 | 8/1990 | Vince et al. | 544/276 |

FOREIGN PATENT DOCUMENTS

| | | | |
|---|---|---|---|
| 0022853 | 1/1989 | Japan | 544/277 |
| 2217320 | 10/1989 | United Kingdom. | |

OTHER PUBLICATIONS

March, J., *Advanced Organic Chemistry*, 3rd Ed., Chap. 4, John Wiley & Sons, New York, NY (1985).
Vince, R., et al., *Biochem. Biophys. Res. Commun.* 156 (2) 1046 (1988).
Trost, et al., *J. Am. Chem. Soc.*, 110, 621 (1988).
*Synthesis*, Sugai, T., et al., 19-22 (1988).
Barrett, et al., J. Organic Chemistry, vol. 51, No. 7, pp. 1012-1015 (1986).
Williams, et al., Tetrahedron Letters, vol. 26(51) pp. 6269-6271 (1985).
Peel, et al., Journal of Organic Chemistry, vol. 56, No. 16, pp. 4990-4993 (1991).
McMurry, et al., J. Org. Chem., vol. 39, No. 2, 259-260 (1974).

*Primary Examiner*—Diana G. Rivers
*Attorney, Agent, or Firm*—Charles T. Joyner

[57] ABSTRACT

This invention relates to a new process for preparing certain optically active cyclopentene derivatives and novel intermediates used in this process. In particular, the invention concerns the synthesis of the 1'R-cis isomer of carbovir, (1'R-cis)-2-amino-1,9-dihydro-9[4-(hydroxymethyl)-2-cyclopenten-1-yl]-6H-purin-6-one, an antiviral agent.

20 Claims, No Drawings

PROCESS FOR THE SYNTHESIS OF CYCLOPENTENE DERIVATIVES OF PURINES

This invention relates to a new process for preparing certain optically active cyclopentene derivatives and novel intermediates used in this process. In particular, the invention concerns the synthesis of the 1'R-cis isomer of carbovir, (1'R-cis)-2-amino-1,9-dihydro-9[4-(hydroxymethyl)-2-cyclopenten-1-yl]-6H-purin-6-one, an antiviral agent.

BACKGROUND OF THE INVENTION

The compound of formula (I):

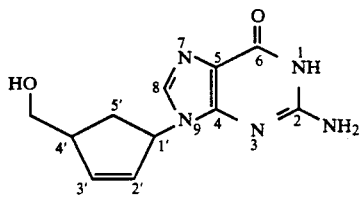

has two optically-active or "chiral" centers, i.e., at the 1' and 4' positions, each of which can exhibit an "R" or an "S" stereo configuration. As will be appreciated by those skilled in this art, a molecule of the compound of formula (I) exists as one of four possible isomers. Stereo configuration and the associated conventions of stereo chemistry are explained in essentially all standard texts on organic chemistry, for example, see March, J., *Advanced Organic Chemistry*, 3d. Ed., Chap 4, John Wiley & Sons, New York (1985).

In the compound of formula (I), there are two isomeric pairs each consisting of two enantiomers (isomers which are mirror images of each other). The isomeric paris are referred to as either "cis" (same side) or "trans" (opposite sides) with respect to the relationship of the non-hydrogen atoms attached to the chiral centers. The isomers may be named by prefixing the compound name with the absolute configuration of one of the chiral centers followed by the "cis" or "trans" designation, i.e., 1'R-cis, 1'R-trans, 1'S-cis and 1'S-trans.

The cis form of formula (I) is depicted below as formula (II):

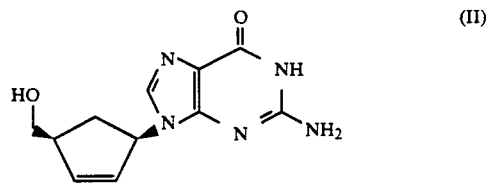

and is meant to represent both cis enantiomers. Thus, the convention of both the 1' and 4' bonds being bold faced is meant to include the enantiomers where the bonds are cis, whether out of the plane of the page or into it.

The racemic mixture (equal mixture) of the 1'R-cis and 1'S-cis enantiomers of the compound of formula (II) is known as carbovir or (±)-carbovir. While racemic carbovir has been reported as having good activity against human immunodeficiency virus (HIV) associated with acquired immune deficiency syndrome (AIDS), the 1'R-cis enantiomer of carbovir, also known as (−)-carbovir, (hereinafter these terms are used interchangeably) has been found to have potent activity against this virus (see Vince, R., et al., *Biochem. Biophys. Res. Commun.*, 156 (2), 1046 (1988)). In view of the high activity of the 1'R-cis enantiomer, it is particularly advantageous to have an efficient method for the synthesis of this enantiomer from relatively inexpensive starting materials.

SUMMARY OF THE INVENTION

We have now found a novel, efficient method for preparing the 1'R-cis enantiomer of carbovir, i.e. (−)-carbovir, starting with 6-oxa-bicyclo[3.1.0]-hex-2-ene and certain 2-amino-6-halopurines. In particular, the present invention provides processes for the synthesis of (−)-carbovir including steps shown in Scheme 1; i.e., (a) reacting the compound of formula (III) or the compound of formula (IIIa) with a compound of formula (IV) in the presence of a Pd(O) complex to yield a compound of formula (V), (b) reacting a compound of formula (V) with an alkoxycarbonylating agent to yield a compound of formula (VI), (c) reacting a compound of formula (VI) by either of

SCHEME 1
SYNTHESIS OF CARBOVIR

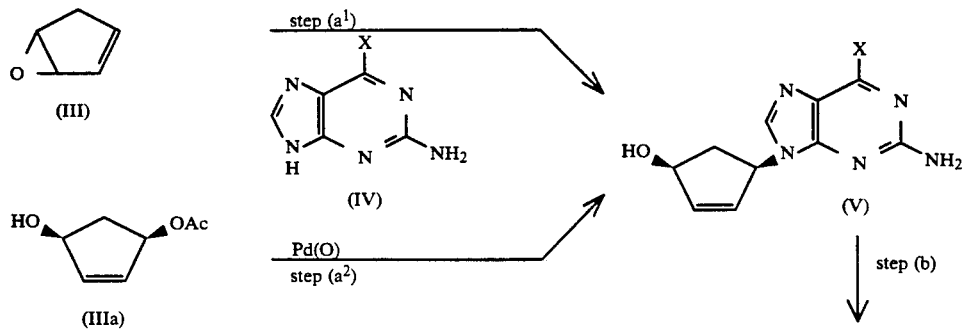

SCHEME 1
SYNTHESIS OF CARBOVIR

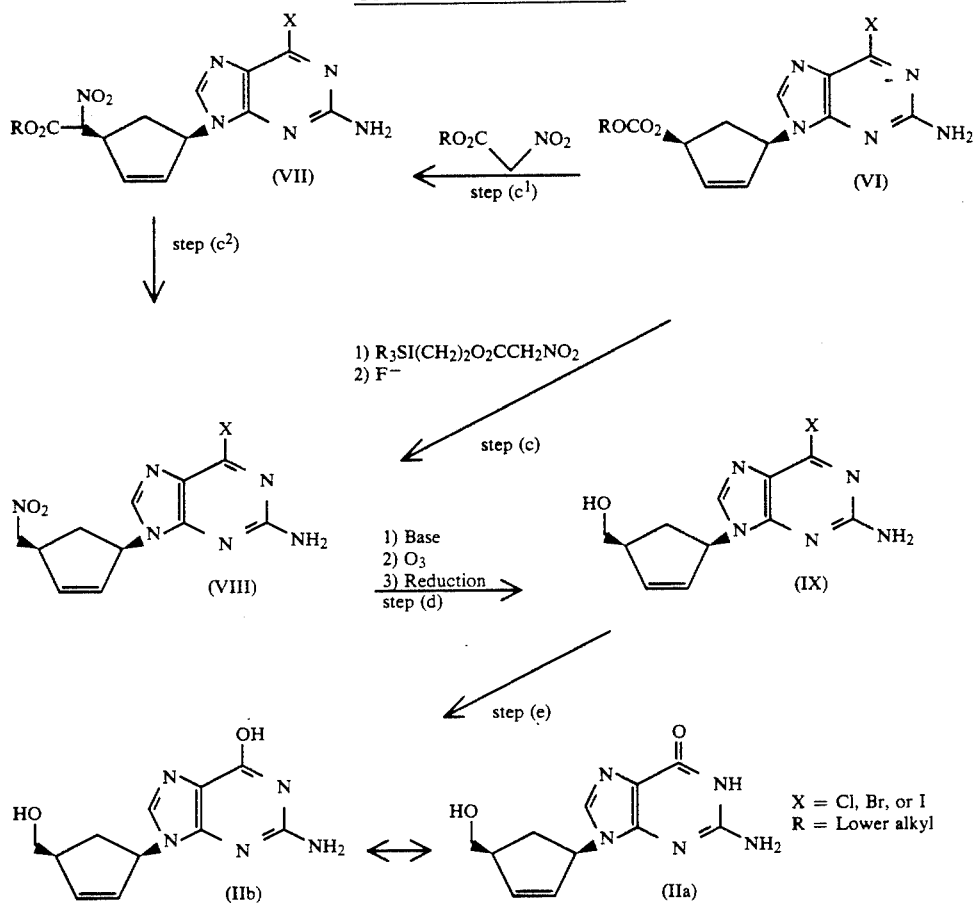

X = Cl, Br, or I
R = Lower alkyl (c) or (c¹) and (c²), to yield a compound of formula (VIII), (d) converting the nitro group of a compound of formula (VIII) to a hydroxy group to yield a compound of formula (IX), and finally (e) converting the chloro, bromo or iodo group of a compound of formula (IX) to a hydroxy compound to yield (−)-carbovir, the compound of formula (II).

In view of its guanine moiety (−)-carbovir exist in two tautomeric forms, (IIa) and (IIb) as shown in Scheme 1. For simplicity, hereinafter (−)-carbovir is depicted in the keto form as shown in formula (IIa), it being understood that it also is represented as the enol form, (IIb), in some publications.

The distribution of the two enantiomers of carbovir may be controlled by selection of the reagents and reaction conditions for the last step, (e) as described by Vince, et al., U.K. Patent Application No. 2217320 A. For example, use of the enzyme adenosine deaminase in step (e) yields (−)-carbovir.

Further embodiments of the present invention are certain novel intermediates derived in synthetic Scheme 1 and the methods for preparing these intermediates.

DETAILED DESCRIPTION OF THE INVENTION

Step (a) of Scheme 1 may be effected by reacting the compound of formula (III), i.e., 6-oxa-bicyclo[3.1.0]-hex-2-ene (also known as 1,2-epoxy-3,4-cyclopentene or cyclopentadiene monoepoxide), with a compound of formula (IV) wherein X is chloro, bromo or iodo, such as, for example, 2-amino-6-chloropurine. This reaction is conducted in the presence of a Pd(O) complex, for example, tetrakis(triphenylphosphine) palladium(O) at ambient temperature (as used herein this term means a temperature range of about 15°-30° C.) in an aprotic solvent in an analogous manner to that taught in J. Am. Chem. Soc., 110, 621 (1988) to yield a compound of formula (V), a racemic mixture of cis enantiomers.

Alternatively the compound of formula (V) can be prepared according to Step (a²) by reacting the compound of formula (IIIa), cis-2-cyclopenten-1,4-diol 4-acetate, with a compound of formula (IV) in the presence of a Pd(O) in an analogous manner and under similar conditions as for step (a¹). The 1S-cis enantiomer of the compound of formula (IIIa) is commercially available or may be prepared by the method taught by T. Sugai and K. Mori, Synthesis, 19-22, (1988). A compound of formula (V) prepared by this route will be in the single enantiomeric form corresponding to that of the compound of formula (IIIa).

It is clear that in Scheme 1, one may utilize racemic mixtures of compounds of formulas (III) or (IIIa) in steps (a¹) and (a²) respectively to yield a racemate of formula (V). However, steps (a¹) and steps (a²) may be carried out with single enantiomers of (III) or (IIIa) respectively or the racemic product of formula (V) may be resolved before proceeding with step (b). In addition, a resolution of enantiomers from a racemate may be carried out on formulas (VI), (VII), (VIII) or even (IX)

before proceeding with the next step. The various aspects of the invention cover all such modification here in meant, unless otherwise indicated, to be inclusive of the reaction of an individual enantiomer.

Step (b) in Scheme 1, which provides the compound of formula (VI) is conveniently executed by treating the racemic mixture of formula (V) or a resolved enantiomer with an alkoxycarbonylating agent, for example, dicarbonic acid dialkyl ester of the formula (ROCO)$_2$O, wherein R is straight or branched chain lower ($C_{1-6}$) alkyl, in the presence of one or more bases, for example, triethylamine (TEA) and dimethyl aminopyridine (DMAP) at ambient temperature in an aprotic solvent, for example, dichloromethane.

By way of step (c), or alternatively the two successive steps (c$^1$) and (c$^2$), the compound of formula (VI) can be converted into the compound of formula (VIII). As shown in step (c), the compound of formula (VI) may be reacted sequentially with the 2-(trialkylsilyl)ethyl ester of nitroacetic acid where the alkyl group may be branched or straight chain of one to six carbons, for example, 2-(trimethylsilyl)ethyl ester of nitroacetic acid, in the presence of a Pd(O) complex (previously described) followed by a source of fluoride ions, for example, cesium fluoride, to obtain the compound of formula (VIII).

Alternatively, the compound of formula (VI) is reacted with a lower, ($C_{1-6}$) straight or branched alkyl nitroacetate, for example, ethyl nitroacetate, in the presence of a Pd(O) complex such as tetrakis(triphenylphosphine) palladium(O) to yield the compound of formula (VII), e.g., a racemic mixture, as shown in step (c$^1$). The compound of formula (VII) is then dealkoxycarboxylated by conventional methods for this type of reaction, in particular, for example, by treatment with sodium chloride in dimethyl sulfoxide (DMSO) to yield the compound of formula (VIII), e.g., a racemic mixture, as shown in step (c$^2$).

Step (d), which constitutes conversion of the nitro function in the compound of formula (VIII) to the corresponding hydroxy function of the compound of formula (IX) constitutes a particularly important aspect of the invention. It is carried out by reacting the compound of formula (VIII) at ambient temperature with a strong, sterically hindered base followed by treatment with ozone and then followed by reaction with a reducing agent capable of yielding the desired hydroxy function. Conveniently an alkali metal or alkaline earth metal tertiary butoxide, for example, potassium tertiary butoxide, may serve as the base and an alkali metal or alkaline earth metal hydride, for example, sodium borohydride, may serve as the reducing agent.

Step (e), which constitutes conversion of a compound of formula (IX) to the 1'R-cis enantiomer of the compound of formula (II), i.e., (−)-carbovir, may be carried out by reacting the compound of formula (IX) sequentially with i) a source of ammonia followed with ii) an enzymatic hydrolysis agent at ambient temperature which selectively yields (−)carbovir, for example, adenosine deaminase.

The novel intermediate compounds disclosed in Scheme 1, which constitute an additional aspect of this invention are those of formulas (V), (VI), (VII) and (VIII).

Particular compounds of formulas (V), (VI), (VII) and (VIII), respectively, are:

a) cis-(±)-4-(2-amino-6-chloro-9H-purin-9-yl)-2-cyclopenten-1-ol;

b) cis-(±)-4-(2-amino-6-chloro-9H-purin-9-yl)-2-cyclopenten-1-yl carbonic acid, methyl ester;

c) [1α,4α(R*)]-(±)-2-amino-6-chloro-9-[[4-nitro-(ethoxycarbonyl)methyl]-2cyclopenten-1yl]-9H-purine and [1α,4α(S*)]-(±)-2-amino-6-chloro-9-[[4-nitro-(ethoxycarbonyl)methyl]-2-cyclopenten-1yl]-9H-purine; and d) cis-(±)-2-amino-6-chloro-9-[4-(nitromethyl)-2-cyclopenten-1-yl]-9H-purine.

The following examples illustrate the aspects of this invention but should not be construed as limitations thereto. The symbols and conventions use in these examples are consistent with those used in the contemporary chemical literature, for example, the *Journal of the American Chemical Society*.

EXAMPLE 1

Cis-(±)-4-(2-amino-6-chloro-9H-purin-9-yl)-2-cyclopenten-1-ol (Formula (V): X=Cl)

To a stirred solution of 2-amino-6-chloro-9H-purine (4.0 g, 23.7 mmol) in dry dimethylsulfoxide (40 mL) at room temperature under N$_2$ is added tetrakis(triphenylphosphine)palladium(O) (0.27 g, 0.23 mmol) and the mixture is stirred for 2 minutes. The solution is cooled to 0° C. and a solution of 6-oxa-bicyclo[3.1.0]hex-2-ene (2.1 g, 25.6 mmol) in dry tetrahydrofuran (20 mL) is added over 15 minutes. The resulting yellow solution is allowed to warm to ambient temperature (about 15°–30° C.) over 3 hours and stirred overnight (about 16 h). The clear, yellow solution is evaporated to a viscous oil which is taken up in dichloromethane (50 mL) and filtered through a small pad of Celite (trademark of Manville Products Corp. for infusorial earth filter aid). The solvent is evaporated and the residue is purified by silica gel chromatography using i) ethyl acetate followed by ii) 10:1 ethyl acetate:methanol as eluent to give cis-(±)-4-(2-amino-6-chloro-9H-purin-9-yl)-2-cyclo-penten-1-ol as a white solid, 5.14 g (86%). M.pt. 160°–162° C. $^1$H nmr: δ7.83 (s, 1H), 6.34 (dt, J$_1$=5.5 Hz, J$_2$=2 Hz, 1H), 5.85 (dd, J$_1$=5.5 Hz, 1H), 5.34 (d, J=10 Hz, 1H), 5.26 (dq, J$_1$=9 Hz, J$_2$=2 Hz, 1H), 5.12 (br s, 2H), 4.85 (br t, J=9 Hz, 1H), 2.97 (ddd, J$_1$=15 Hz, J$_2$=9 Hz, J$_3$=7 Hz, 1H), 2.13 (br d, J=15 Hz, 1H).

EXAMPLE 1-A 4R-(2-Amino-6-chloro-9H-purin-9-yl)-2-cyclopenten-1S-ol

To a stirred solution of 2-amino-6-chloropurine (0.2 g, 1.18 mmol) in dry DMSO (2 mL) at room temperature under N$_2$ was added potassium tert-butoxide (135 mg, 1.2 mmol) and the mixture was stirred for 20 min. Tetrakis(triphenylphosphine)palladium (O) (50 mg, 0.04 mmol) was added and the mixture was cooled to 0° C. To this mixture was added a solution of (1R,3S)-4-cyclopentene-1,3-diol 1-acetate (0.17 g, 1.19 mmol) in dry tetrahydrofuran (2 mL) over 10 min. and the resulting mixture was stirred at room temperature for 18 h. The solvents were removed by evaporation at reduced pressure and the residue was slurried in dichloromethane (approx.25 mL) and filtered. The filtrate was evaporated and the residue was purified by chromatography on silica gel using i) EtOAc followed by 10:1 EtOAc:MeOH as eluent to give 4R-(2-Amino-6-chloro-9H-purin-9-yl)-2-cyclopenten-1S-ol (174 mg, 58%).

EXAMPLE 2

Cis-(±)-4-(2-amino-6-chloro-9H-purin-9-yl)-2-cyclopenten-1-yl carbonic acid, methyl ester (Formula (VI): X=Cl)

Dicarbonic acid, dimethyl ester (2 g, 15 mmol) is added dropwise to a stirred solution of cis-(±)-4-(2-amino-6-chloro-9H-purin-9-yl)-2-cyclopenten-1-ol (2.0 g, 8 mmol) and 4-dimethylaminopyridine (3 mg) in dry dichloromethane (20 mL) at ambient temperature and stirring is continued for 20 minutes. Additional dicarbonic acid, dimethyl ester (2 g) is added and the mixture is stirred for a further 20 minutes whereupon the mixture becomes clear. The solvent is evaporated and the residue is taken up in dichloromethane (20 mL) and treated with dicarbonic acid, dimethyl ester (2 g).

This evaporation/retreatment with dicarbonic acid, dimethyl ester sequence is repeated until no starting material remained by thin layer chromatography. The solution is finally evaporated to afford cis(±)-4-(2-amino-6-chloro-9H-purin-9yl)-2-cyclopenten-1-yl carbonic acid, methyl ester as a white solid, (2.36 g, 96%). $^1$H nmr, $\delta$ 7.83 (s, 1H), 6.37 (dt, $J_1$=5.5 Hz, $J_2$=2 Hz, 1H), 6.18 (dd, $J_1$=5.5 Hz, $J_2$=2 Hz, 1H), 5.66 (m, 1H), 5.54 (m, 1H), 5.22 (br s, 2H), 3.80 (s, 3H), 3.10 (dt, $J_1$=15 Hz, $J_2$=8 Hz, 1H), 2.00 (dt, $J_1$=15 Hz, $J_2$=3 Hz, 1H).

EXAMPLE 3

Cis-(±)-2-amino-6-chloro-9-]4-(nitromethyl)-2-cyclopenten-1-yl]-9H-purine (Formula (VIII): X=Cl)

A. Nitroacetic acid, 2-(trimethylsilyl)ethyl ester

To a stirred solution of nitroacetic acid ethyl ester (5.0 g, 37.6 mmol) and 2-(trimethylsily)ethanol (7.27 g, 61 mmol) in dry benzene (100 mL) is added titanium tetraisopropoxide (1.05 q, 3.69 mmol) and the mixture is heated at reflux for 1 hour. The solution is cooled to 40° C. and water (2 mL) is added and stirring is continued for 10 minutes at room temperature. The solvents are evaporated and the residue is taken up in dichloromethane and dried over anhydrous magnesium sulfate. The mixture is filtered through a small pad of Celite and the solvent is evaporated. The residue is purified by distillation to givè nitroacetic acid, 2-(trimethylsily)ethyl ester (6.10 g, 79%) as a colorless liquid. B.pt. 90°-95° C./0.3 mmHg.

B.
Cis-(±)-2-amino-6-chloro-9-[4-(nitromethyl)-2-cyclopenten-1-yl]-9H-purine

To a stirred solution of cis-(±)-4-(2-amino-6-chloro-9H-purin-9-yl)-2-cyclopenten-1-yl carbonic acid, methyl ester (1.95 g, 6.3 mmol) and nitroacetic acid, 2-(trimethylsilyl)ethyl ester (1.30 g, 6.3 mmol) in dry tetrahydrofuran (30 mL) at ambient temperature under N$_2$ is added tetrakis(triphenylphosphine)palladium(O) (0.3 g, 0.26 mmol) and the mixture is stirred for 30 minutes. The solvent is evaporated to leave an orange oil (2.76 g). This oil is dissolved in dry acetonitrile (20 mL) and cesium fluoride (2.0 g, 13 mmol) is added. The mixture is heated at 50° C. under N$_2$ for 24 h. The resulting suspension is cooled to ambient temperature, diluted with dichloromethane (30 mL) and filtered through a small pad of Celite. The solvent is evaporated and the residue is purified by silica gel chromatography using i) 1:1 hexane:ethyl acetate and ii) ethyl acetate as eluent to give cis-(±)-2-amino-6-chloro-9-[4-(nitro-methyl)-2-cyclopenten-1-yl]-9H-purine, (1.15 g, 62%). $^1$H nmr $\delta$ 7.72(s, 1H), 6.14 (dt, $J_1$=5.5 Hz, $J_2$=2 Hz, $J_1$=5.5 Hz, $J_2$=2 Hz, 1H), 5.98 (dt, $J_1$=5.5 Hz, $J_2$=2 Hz, 1H), 5.56 (m, 1H), 5.07 (br s, 2H), 4.61 (dd, $J_1$=12.5 Hz, $J_2$=6.5 Hz, 1H), 4.56 (dd, $J_1$=12.5 Hz, $J_2$=7.5 Hz, 1H), 3.59 (m, 1H), 2.96 (dt, $J_1$=14.5 Hz, $J_2$=8.5 Hz, 1H), 1.87 (dt, $J_1$=14.5 Hz, $J_2$=6.5Hz, 1H).

EXAMPLE 4

[1α,4α(R*)]-(±)-2-amino-6-chloro-9-[[4-nitro-(ethoxycarbonyl)methyl]-2-cyclopenten-1-yl]-9H-purine and [1α,4α(S*)]-(±)-2-amino-6-chloro-9-[[4-nitro-(ethoxycarbonyl)methyl]-2-cyclopenten-1-yl]-9H-purine (Formula (VII): X=Cl)

To a stirred solution of cis-(±)-4-(2-amino-6-chloro-9H-purin-9-yl)-2-cyclopenten-1-yl carbonic acid, methyl ester (1.50 g, 4.85 mmol) and nitroacetic acid, ethyl ester (0.68 g, 5.11 mmol) in dry tetrahydrofuran (20 mL) at ambient temperature under N$_2$ is added tetrakis (triphenylphosphine)paladium(O) (0.15 g, 0.13 mmol) and the resulting yellow solution is stirred for 90 minutes. The solvent is evaporated and the residue is purified by silica gel chromatography using as eluent, i) 1:1 hexanes:ethyl acetate followed by 100% ethyl acetate to give [1α,4α(R*)]-(±)-2-amino-6-chloro-9-[[4-nitro(ethoxycarbonyl)methyl]-2-cyclopenten-1-yl]-9H-purine and [1α,4α(S*)]-(±)-2-amino-6-chloro-9-[[4-nitro(ethoxycarbonyl)-methyl]-2-cyclopenten-1-yl]-9H-purine, (1.65 g, 93%) as an off white solid. The product is an inseparable mixture of diastereoisomers. $^1$H nmr, $\delta$ 7.73 and 7.72 (2s, 1H), 6.11 and 6.07 (2dt, $J_1$=5.5 Hz, $J_2$=2 Hz, 1H), 5.95 (m, 1H), 5.60 and 5.58 (2d, J=5.5 Hz, 1H), 5.53 (m, 1H), 5.26 (br s, 2H), 4.29 (m, 2H), 3.77 (m, 1H), 2.97 (m, 1H), 2.05 and 1.94 (2dt, $J_1$=14.5 Hz, $J_2$=6 Hz, 1H), 1.29 (m, 3H).

EXAMPLE 5

Cis-(±)-2-amino-6-chloro-9-[4-(nitromethyl)-2-cyclopenten-1-yl]-9H-purine (Formula (VIII): X=Cl)

A mixture of [1α,4α(R*)]-(±)-2-amino-6-chloro-9-[[4-nitro-(ethoxycarbonyl)methyl]-2-cyclopenten-1-yl]-9H-purine and [1α,4α(S*)]-(±)-2-amino-6-chloro-9-[[4-nitro(ethoxycarbonyl)-methyl]-2-cyclopenten-1-yl]-9H-purine from Example 4 (1.13 g, 3.08 mmol), sodium chloride (1.0 g, 17 mmol) and water (0.2 mL, 20 mmol) in dimethylsulfoxide (15 mL) is heated at approx. 150° C. for 4 hr. The solvent is evaporated at reduced pressure and the black residue is taken up in ethyl acetate and filtered through a small plug of Celite. The filtrate is washed with saturated sodium chloride solution and dried over anhydrous magnesium sulfate. The solvent is evaporated to leave cis-(±)-2-amino-6-chloro-9-[4-(nitromethyl)-2-cyclopenten-1-yl]-9H-purine as a light, brown solid (0.66 g, 66%). A sample is purified by silica gel chromatography using ethyl acetate as eluent. Physical and spectral data as described in example 3.

EXAMPLE 6

Cis-(±)-2-amino-6-chloro-9-[[4-(hydroxymethyl)-2-cyclopenten-1-yl]-9H-purine (Formula (IX): X=Cl)

To a stirred solution of cis-(±)-2-amino-6-chloro-9-[4-(nitromethyl)-2-cyclopenten-1-yl]-9H-purine from Example 5 (0.085 g, 0.29 mmol) in dry tetrahydrofuran (2 mL) at −20° C. under N$_2$ is added potassium tertiary butoxide (0.034 g, 0.3 mmol) and the mixture is stirred for 15 minutes. Dry methanol (1 mL) is added and the mixture is cooled to −78° C. In a separate flask, ozone is bubbled through dry a saturated solution. This saturated solution of ozone is then added to the solution of nitronate anion and the mixture is stirred at −78° C. for 10 minutes. Sodium borohydride (0.025 g, 0.65 mmol) is added to the solution and the cooling bath is removed. The solution is allowed to warm to ambient temperature over 30 minutes. The solvent is evaporated under reduced pressure and the residue is taken up in water (2 mL) and carefully neutralized using aqueous sodium hydroxide solution (2N). The aqueous solution is extracted with dichloromethane and the organic extracts are washed with saturated sodium sulfate.

Evaporation of the solvent, followed by purification by silica gel chromatography using i) 1:1 hexanes:ethyl acetate and ii) ethyl acetate as eluent gave recovered cis-(±)-2-amino-6-chloro-9-[4-(nitromethyl)-2-cyclopenten-1-yl]-9H-purine (0.023 g, 27%) followed by cis-(±)-2-amino-6-chloro-9-[4-(hydroxymethyl)-2-cyclopenten-1-yl]-9H-purine, (0.024 g33%). $^1$H nmr δ 7.89 (s, 1H), 6.14 (dt, $J_1=5.5$ Hz, $J_2=2$ Hz), 5.79 (dt, $J_1=5.5$ Hz, $J_2=2$ Hz), 5.51 (m, 1H), 5.18 (br s, 2H), 3.84 (dd, $J_1=10.5$ Hz, $J_2=4$ Hz, 1H), 3.73 (dd, $J_1=10.5$ Hz, $J_2=4$ Hz, 1H), 3.09 (m, 1H), 2.79 (dt, $J_1=14.5$ Hz, $J_2=9$ Hz, 1H), 1.97 (dt, $J_1=14.5$ Hz, $J_2=5.5$ Hz, 1H).

EXAMPLE 7

(1'R-cis)-2-amino-1,9-dihydro-9-[4-(hydroxymethyl)-2-cyclopenten-1-yl]-6H-purin-6-one (Formula (II))

A.

Cis-(±)-2,6-diamino-9-[4-hydroxymethyl)-2-cyclopentenl-yl]-9H-purine

Liquid ammonia is passed into a solution of cis-(±)-2-amino-6-chloro-9-[4-(hydroxymethyl)-2-cyclopenten-1-yl]-9H-purine (0.265 g, 1 mmol) in methanol (10 mL) at −80° C. in a bomb. The bomb is sealed and heated at 75° C. for 48 hours. The bomb is cooled to room temperature and the ammonia and methanol are evaporated. The residue is purified by silica gel chromatography using 15:1 chloroform methanol as eluent to give cis-(±)-2,6-diamino-9-[4-(hydroxymethyl)-2-cyclopenten-1-yl]-9H-purine (0.196 g, 80%). M.pt. 152°–155° C. MS (30 ev, 200° C.): m/e 246 (M+), 229 (M+−17), 216 (M+-30).

B. To a solution of cis-(±)-2,6-diamino-9-[4-(hydroxymethyl)-2-cyclopenten-1-yl]-9H-purine (0.10 g, 0.41 mmol) in buffer (3 mL of 0.05M potassium phosphate, pH 7.4) at 25° C. is added adenosine deaminase (40 units, Sigma, Type VI, calf intestinal mucosa). After three days of incubation at room temperature the precipitate which forms is collected by filtration. The filtrate is concentrated to 1.5 mL and refrigerated for 2 days. The solid formed was collected by filtration and the combined solids are recrystallized from water to give 1'R-cis-2-amino-1,9-dihydro-9-[4-(hydroxymethyl)-2-cyclopenten-1-yl]-6H-purin-6-one as a white solid. M.pt. 269°–272° C.; [α]$_D$-62.1(c 0.3 methanol)

We claim:

1. A method for preparing of a compound of formula (IX),

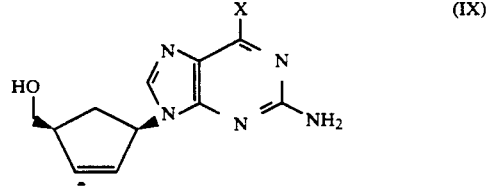

wherein X is chloro, bromo or iodo, comprising reacting a compound of formula (VIII),

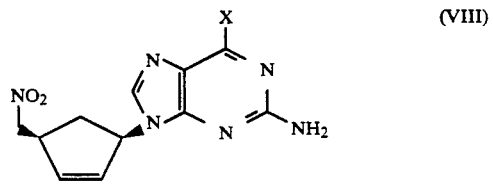

with a strong, sterically hindered base followed by ozone and reacting the product with a reducing agent to yield the compound of formula (IX).

2. The method of claim 1 wherein the strong, sterically hindered base is an alkali metal or alkaline earth metal tertiary butoxide and the reducing agent is an alkali metal or alkaline earth metal hydride.

3. The method of claim 1 wherein the strong, sterically hindered base is potassium tertiary butoxide and the reducing agent is sodium borohydride.

4. The method of claim 1 wherein X is chloro.

5. A compound of formula (VIII),

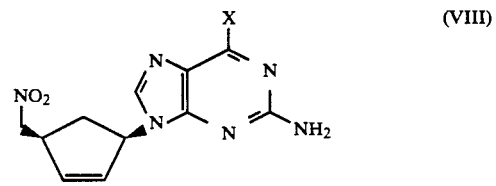

wherein X is chloro, bromo or iodo.

6. The compound of claim 5 which is cis-(+)-2-6-chloro-9-[4-(nitromethyl)-2-cyclopenten-1-yl]-9H-purine.

7. A compound of the following formula (VII),

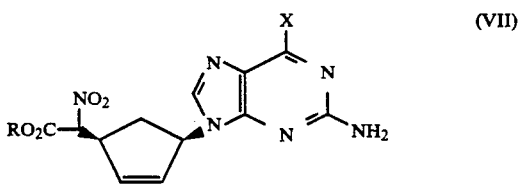

wherein X is chloro, bromo or iodo and R is lower ($C_{1-6}$) alkyl.

8. The compound of claim 7 which is [1α,4α(R*)]-(±)-2-amino-6-chloro-9-[[4-nitro(ethoxycarbonyl)methyl]-2-cyclopenten-1yl]-9H-purine or [1α,4α(S*)]-(±)-2-amino-6-chloro-9-[[4-nitro(ethoxy-carbonyl)methyl]-2-cyclopenten-1yl]-9H-purine or a mixture thereof.

9. A compound of formula (VI),

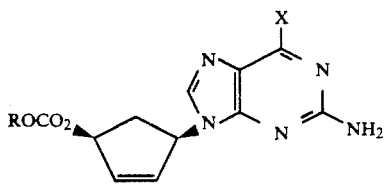

wherein X is a chloro, bromo or iodo and R is lower (C₁₋₆) alkyl.

10. The compound of claim 9, wherein said compound is Cis-(±)-4-(2-amino-6-chloro-9H-purin-9-yl)-2-cyclopenten-1-yl carbonic acid, methyl ester.

11. A compound of formula (V),

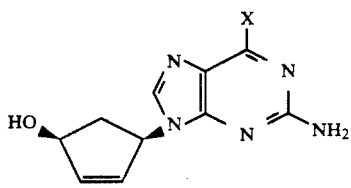

wherein X is a chloro, bromo or iodo.

12. The compound of claim 11 which is cis-(±)-4-(2-amino-6-chloro-9H-purin-9-yl)-2-cyclopenten-1-ol.

13. The method for the synthesis of (−)-carbovir, the 1' R-cis enantiomer of the compound of formula (II),

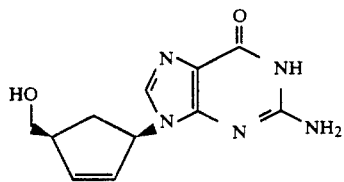

(a) which comprises: reacting a compound of formula (VIII),

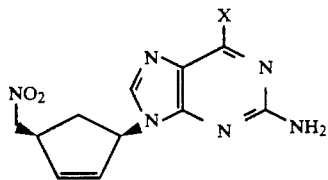

wherein X is chloro, bromo or iodo, with a strong, sterically hindered base followed by ozone and reacting the product with a reducing agent to yield a compound of formula (IX), and

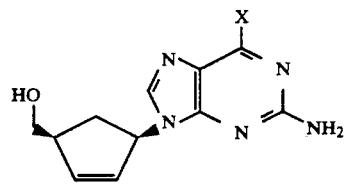

(b) reacting a compound of formula (IX) sequentially with a source of ammonia followed by an enzymatic hydrolysis agent which selectively yields (−)-carbovir.

14. The method of claim 13 wherein X is chloro and the enzymatic hydrolysis agent is adenosine deaminase.

15. The method of claim 13, wherein the compound of formula (VIII) is prepared by decarbonylating a compound of formula (VII),

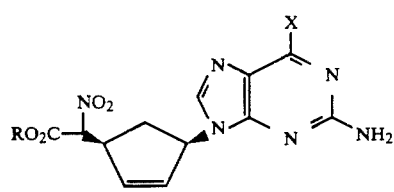

wherein X is chloro, bromo or iodo and R is lower (C₁₋₆) alkyl.

16. The method of claim 15 wherein X is chloro, R is methyl or ethyl and the enzymatic hydrolysis agent is adenosine deaminase.

17. The method of claim 13, wherein the compound of formula (VIII) is prepared by reacting of a compound of formula (VI),

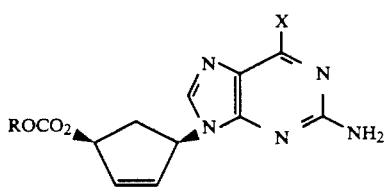

wherein X is chloro, bromo or iodo and R is lower (C₁₋₆) alkyl, reacting a compound of formula (VI) with R₃Si(CH₂)₂O₂CCH₂NO₂ in the presence of a Pd(O) complex followed by treatment with a source of fluoride ions 18. The method of claim 15, wherein the compound of formula (VII) is prepared by reacting a compound of formula (VI),

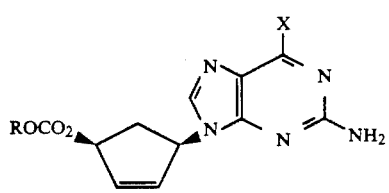

wherein X is chloro, bromo or iodo and R is lower (C₁₋₆) alkyl with RO₂CCH₂NO₂ in the presence of a Pd(O) complex.

19. The method of claim 17, wherein said compound of formula (VI) is prepared by reacting a compound of formula (V),

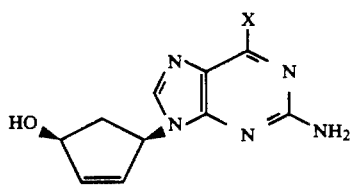

wherein X is chloro, bromo or iodo, with (ROCO)₂O, wherein R is lower (C₁₋₆) alkyl.

20. The method of claim 19, wherein said compound of formula (V) is prepared by reacting the compound of formula (III) with a compound of formula (IV),

 (III)
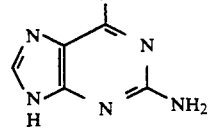 (IV)
wherein X is chloro, bromo or iodo, in the presence of a Pd(O) complex.
* * * * *